United States Patent
Jamison et al.

(10) Patent No.: US 7,358,221 B1
(45) Date of Patent: Apr. 15, 2008

(54) METATHESIS DEPOLYMERIZABLE SURFACTANTS

(75) Inventors: Gregory M. Jamison, Albuquerque, NM (US); David R. Wheeler, Albuquerque, NM (US); Douglas A. Loy, Tucson, AZ (US); Blake A. Simmons, San Francisco, CA (US); Timothy M. Long, Evanston, IL (US); James R. McElhanon, Manteca, CA (US); Kamyar Rahimian, Albuquerque, NM (US); Chad L. Staiger, Albuquerque, NM (US)

(73) Assignee: Sandia Corporation, Livermore, CA (US)

( * ) Notice: Subject to any disclaimer, the term of this patent is extended or adjusted under 35 U.S.C. 154(b) by 224 days.

(21) Appl. No.: 11/475,267

(22) Filed: Jun. 26, 2006

Related U.S. Application Data (63) Continuation-in-part of application No. 10/866,474, filed on Jun. 10, 2004, now abandoned.

(51) Int. Cl.
*C11D 3/37* (2006.01)

(52) U.S. Cl. .................................... 510/476; 510/475
(58) Field of Classification Search ............... 510/475, 510/476

See application file for complete search history.

(56) References Cited

U.S. PATENT DOCUMENTS

2002/0156207 A1* 10/2002 Imuta et al. ................ 526/127

* cited by examiner

*Primary Examiner*—John R. Hardee
(74) *Attorney, Agent, or Firm*—Donald A. Nissen (57) ABSTRACT

A class of surfactant molecules whose structure includes regularly spaced unsaturation in the tail group and thus, can be readily decomposed by ring-closing metathesis, and particularly by the action of a transition metal catalyst, to form small molecule products. These small molecules are designed to have increased volatility and/or enhanced solubility as compared to the original surfactant molecule and are thus easily removed by solvent extraction or vacuum extraction at low temperature. By producing easily removable decomposition products, the surfactant molecules become particularly desirable as template structures for preparing meso- and microstructural materials with tailored properties.

26 Claims, 7 Drawing Sheets

P = hydrophilic

▬ = metathesis-reactive group

◆ = Gemini tether

METATHESIS DEPOLYMERIZABLE SURFACTANTS

CROSS-REFERENCE TO RELATED APPLICATIONS

This application is a Continuation-in-Part of prior application Ser. No. 10/866,474 filed Jun. 10, 2004, now abandoned, from which benefit is claimed.

STATEMENT OF GOVERNMENT INTEREST

This invention was made with Government support under contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

FIELD OF THE INVENTION

This invention is directed to a class of surfactant compounds that are designed such that the action of catalytic metathesis decomposition produces products having increased volatility or enhanced solubility at mild temperatures.

BACKGROUND OF THE INVENTION

Surfactants constitute a class of amphiphilic molecules whose physical and chemical properties provide the opportunity to manipulate conditions for the controlled emulsion polymerization of a variety of functional monomers. The resultant soluble macromolecules reflect, in part, physical and chemical properties derived % from the surfactant-mediated polymerization conditions, including molecular weight and polydispersity. Surfactants also allow for the sequestration and separation of valuable compounds from incompatible or dissimilar media, e.g., detergent and waste recovery applications, wetting agents, thickeners, tertiary petrochemical recovery and processing.

The ability of surfactants to arrange into ordered, low energy spherical micelles, planar lamellae or higher ordered structures, e.g., stacked lamellae, tubes/rods, can be used to provide a templating surface from which ordered meso- and microstructural materials with tailored properties can be generated. The physical arrangement of the final material, such as zeolites, nanoparticles, and biomaterials, reflects the ordering of the template structure. The proper selection of conditions, e.g., solvent media and temperature, allows for the control not only of the growth of such structures but also their properties such as electronic activity, porosity and permeability.

While ordered surfactants can provide a desirable template structure, realizing the desired properties of the final material requires that the surfactant template be removed. The process of removal can present a significant technical challenge since the surfactant materials are often large and relatively non-volatile amphiphiles that are difficult to remove by means other than harsh thermal or corrosive chemical treatments with attendant damage to the final material.

Some examples of surfactants exist in the literature which may be degraded under mild chemical conditions. Generally, a change in the pH of a system has been used to degrade surfactants with acid-sensitive functionalities, such as dioxolanes (see (a). Ono, D.; Masuyama, A.; Okahara, M. *J. Org. Chem.* 1990,-55, 4461; (b) Jaeger, D. A.; Li, B.; Clark, Jr., T. C. *Langmuir* 1996, 12, 4314; (c) Jaeger, D. A.; Wettstein, J.; Zafar, A. *Langmuir* 1998, 14, 1940; (d) Piasecki, A.; Sokolowski, A.; Burczyk, B.; Gancarz, R.; Kotlewska, U. *Langmuir* 1997, 13, 143). Acid cleavable surfactants have been successfully utilized for removal of detergents used in preparation of hydrophobic protein samples for MALDI-MS analysis (see (a) Caprioli, R. M.; Porter, N. A.; Norris, J. L. WIPO Patent 2002, WO 02/097393 A2. (b) Norris, J. L.; Porter, N. A.; Caprioli, R. M. *Anal. Chem.* 2003, 75, 6642), and a recent report details the use of condensable surfactants with masked functionalities, developed for the production of templated organo-silicates with precise interior surface functionalities which are exposed by partial surfactant degradation via hydrolysis after vitrification and calcinations (Zhang, Q.; Ariga, K.; Okabe, A.; Aida, T. *J. Am. Chem. Soc.* 2004, 126, 988).

Base-sensitive surfactants include functional groups such as esters or 13-ammonium ketones (see (a) Jaeger, D. A.; Finley, T.; Walter, M. R.; Martin, C. A. *J. Org. Chem.* 1986, 51., 3956. (b) Lindstedt, M.; Allenmark, S.; Thompson, R. A.; Edebo, L. *Antimicrob. Agents Chemother.* 1990, 34, 1949). Efforts toward surfactants which allow for reversible control of surface activity and interfacial surface tension through incorporation of redox-active ferrocenyl moieties have also been reported (see (a) Gallardo, B. S.; Hwa, M. J.; Abbott, N. L. *Langmuir* 1995, 11, 4209; (b) Gallardo, B. S.; Metcalfe, K. L.; Abbott, N. L. *Langmuir* 1996, 12, 4116; (c) Bennett, D E.; Gallardo, B. S.; Abbott, N. L. *J. Am. Chem. Soc.* 1996, 118, 6499; (d) Gallardo, B. S.; Abbott, N. L. *Langmuir* 1997, 13, 203).

Surfactants sensitive to non-chemical stimuli include photosensitive azosulfonates (Mezger, T.; Nuyken, O.; Meindl, K.; Wokaun, A. *Prog. Org. Coat.* 1996, 29, 147) and thermally sensitive amine oxides (Hayashi, Y.; Shirai, F.; Shimzu, T.; Nagano, Y.; Teramura, K. *J. Am. Oil Chemists Soc.* 1985, 62, 555).

The examples above require conditions, either chemical or physical, that may be adverse for removing the surfactant template without damage to any hierarchical material structure and are not applicable under conditions requiring neutral pH, or those conditions where oxidative or reductive environments are unsuitable for material processing.

SUMMARY OF THE INVENTION

Accordingly, the present invention pertains to a family of surfactant molecules which incorporate regularly spaced unsaturation in their hydrocarbon tails. The disposition of the organic unsaturation allows for the degradation of the surfactant materials into easily removable products by the action of transition metal catalysts under mild reaction conditions, such as metathesis depolymerization of the hydrocarbon tail fragment of the surfactant.

The decomposition of the surfactants described herein can be by ring-closing metathesis or acyclic diene metathesis (ADMET) by the action of catalytic quantities of metathesis-active transition metal catalysts to form small molecule products (typically, but not restricted to, cycloalkenes) having increased volatility and/or enhanced solubility as compared to the original surfactant molecule; as such, the decomposition products are thus easily removable by solvent extraction or vacuum extraction at low temperature. Because surfactant molecules of the invention can be readily decomposed into easily removable product molecules, these surfactant molecules are desirable as template structures for preparing the ordered meso- and microstructural materials with tailored properties, as discussed above.

The present invention provides, in part, compositions including, but not limited to, novel cleavable surfactants and methods for preparing cleavable surfactants containing polyene hydrocarbon tails and degrading the surfactants under mild, controlled reaction conditions in the presence of active transition metal catalysts.

In one embodiment of the invention, the surfactant can comprise a single hydrophobic, metathesis-reactive oligodienyl group bound to a single hydrophilic group that together form a monomeric surfactant. Included in this group of surfactants are cationic, anionic, zwitterionic and/or non-ionic surfactants. Specific examples of the preparation of the novel surfactant molecules are provided in which the hydrophobic tail fragment of the surfactant is composed of oligo-(1,5-pentadienyl), oligo-(1,6-hexadienyl) or oligo-(1,7-heptadienyl) repeat units.

In another embodiment of the invention, certain compositions which can yield degradation products that can themselves be surface active compounds are described. In such embodiment, the novel surfactants can include the family of Gemini surfactants, wherein one or more hydrophilic groups are tethered to one or more hydrophobic groups, and wherein the hydrophilic groups can include one or more ionic or nonionic surfactant materials such as those discussed above. Within this embodiment, the metathesis-active oligodienyl functionality may be a terminal chain or act as the Gemini tethering group situated between two hydrophilic groups, two hydrophobic groups or between the junctions of two monomeric surfactants. Gemini surfactants are particularly desirable as surfactant template materials because of their ability to emulsify at low micelle concentrations when compared to the monomeric precursors from which they are derived. Furthermore, these Gemini surfactants could degrade into smaller surfactant subcomponents that still display the capability to organize into ordered phases. Thus, catalytic disruption of the "bridging" chemical tether provides for modifying surfactant behavior without completely destroying the emulsifying capabilities of the system and the requisite templates they provide.

A further aspect of the present invention provides for the degradation of a polyene-containing surfactant by metathesis-active transition metal catalyst(s), or metathesis-active co-catalyst systems that yield cycloalkene products through the action of the catalysts alone, without the need for secondary reactants or initiators.

Yet another aspect of the present invention embodies the degradation of the polyene-containing surfactant by transition metal catalyst(s) which yield low molecular weight linear alkene products through the action of the catalysts in the presence of external initiating reactants via acyclic diene metathesis degradation.

DETAILED DESCRIPTION OF THE INVENTION

The present invention is directed to a novel class of surfactant molecules that possess a structure that can be readily decomposed by ring-closing metathesis, and particularly by the action of a transition metal catalyst, to form small molecule products that have increased volatility and/or enhanced solubility as compared to the original surfactant molecule and are thus easily removable by solvent extraction or vacuum extraction at low temperature.

The basic structure of a surfactant molecule of the invention as illustrated generally in (1) below in which A comprises a hydrophilic head group, B a linker group, comprising at least one alkyl or aryl group, and a tail group C, wherein C is an unsaturated hydrocarbon having the general structure (2)

wherein $R^1$, $R^2$, $R^3$, and $R^4$ are each independently, hydrogen, straight or branched chain alkyl groups, including heteroatom functionalities, or cyclic alkyl chains; n is at least 2; and a is 1 to 6. In surfactant molecule (1) m is equal or greater than 1; and p is at least 1.

The head group A can be a polar group and can include alkoxides, alkyl sulfides, phenolates, thiophenolates, carboxylates, sulfates, sulfonates including sulfated polyethylenated alcohols, sulfated triglyceride oils, sulfosuccinates, phosphates, phosphonates, polyphosphonates, carbonates and borates.

The head group can also include amines such as —NR'R"R'''$^+$, —P R'R"R'''$^+$, —SR'R"$^+$, guanidnium, pyridinium, or other quaternized heterocyclic amines wherein R', R", R''' each represent hydrogen or any aliphatic, cyclic or aromatic organic group with or without further substitution.

The head group can be polyoxyethylenated alkyl phenol, tertiary acetylenic glycol, pyrrolidone, alkylglycoside, or a zwitterion.

The linker group B can be an unsubstituted $(CH_2)_n$ or a branched $(CRR')_n$ linear or cyclic alkyl chain, wherein n>0. The linker group can also be an unsubstituted or multiply substituted aromatic ring system (noninclusive of the hydrophilic head group and the hydrophobic tail fragment) wherein the substitution is selected from a group consisting of alkyl, halogen, heteroatom-containing alkyl or combinations thereof and wherein the polar head group(s) and hydrophobic tail are arranged ortho, meta- or para- about the linker group. The linker group can be a chain of two of more aromatic rings subject to the substitution patterns described above. The linker group can be a partially fluorinated or fully fluorinated moiety. In a preferred embodiment of the invention, the linker group is as short as possible in order to facilitate the catalytic degradation of the surfactant molecule into small and soluble molecules, The tail group C can be any metathesis-active alkene-containing organic moiety capable of degrading upon exposure to suitable catalyst systems and reaction conditions. In a preferred embodiment, the hydrophobic degradable tail section contains an unsubstituted or substituted oligo-(1,5-pentadienyl), oligo-(1,6-hexadienyl) or oligo-(1,7-heptadienyl) group; no limitation to the pattern or degree of substitution on the metathesis-active portion of the surfactant is implied, and substituents can include straight chain alkyl or branched alkyl groups, straight chain alkyl or branched alkyl groups containing heteroatoms, unsubstituted or multiply substituted aromatic groups, unsubstituted or multiply substituted aromatic groups containing heteroatoms. In a particularly preferred embodiment, the degradable fragment may be partially or fully fluorinated.

The moiety comprising B and C can be any single (or combination of) alkyl group(s) with at least one group being the metathesis-degradable oligodienyl tail.

The integer m, encompassing both the linker and tail portions of the surfactant molecule can be greater than or equal 1. There can be more than one metathesis-active tail group is which case m is greater than 1.

The value of n can be greater than or equal 1 and preferably sufficiently large to realize optimal surface active behavior.

The value of p, the number of head groups attached to the linker group, is at least 1. However, since there can be more than one head group, p can be greater than 1.

In the instance that the hydrophobic tail does not possess regularly disposed unsaturated alkenes, then the hydrophobic tail may be an organic chain bearing one or more alkene functional groups, in which case decomposition may be performed under ADMET (Acyclic Diene Metathesis)-type decomposition reaction conditions. The alkene containing chain may typically include, but is not restricted to, alkene-containing homo- or copolymer moieties such as polybutadiene, polyisoprene, polystyrene, etc.

Preferred surfactant embodiments of the invention are dipotassium heneicosa-2,8,14,20-tetraenyl malonate, 13-(triphenylphosphonium)trideca-1,7-dienyl iodide, 19-(triphenylphosphonium)trideca-1,7-dienyl iodide and 19-(N,N,N-trimethylammonium)nonadeca-1,7,13-trienyl iodide.

Figure 1:
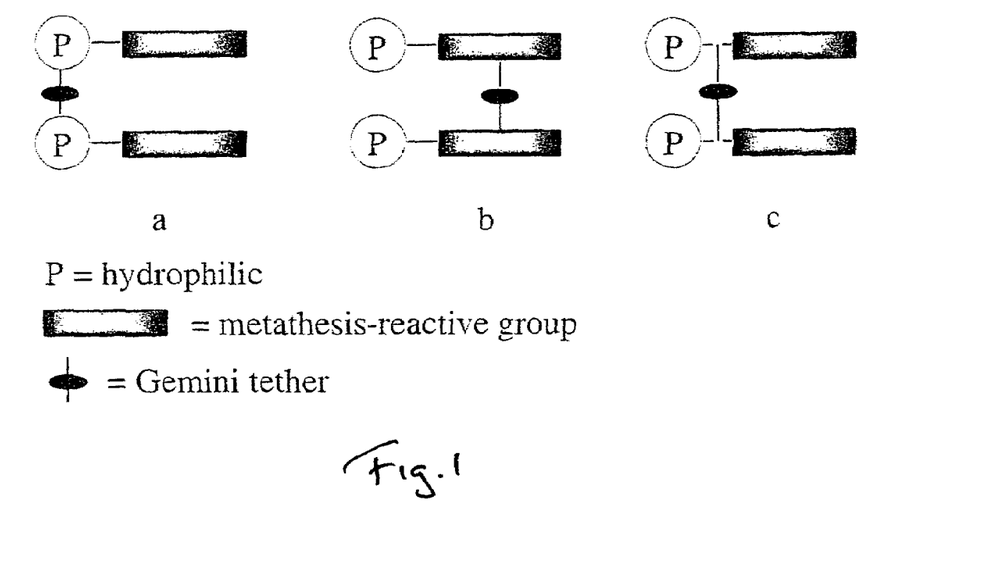
FIGS. 1a-1c show a Gemini surfactant molecule with different attachment points.

In a second embodiment of the invention, illustrated generally in FIGS. 1a-1c, the surfactant molecule is a dimeric or Gemini, surfactant. The Gemini surfactant molecule comprises two spaced apart surfactant molecules, of the type represented by formula (I) above, joined by a tethering group that can be situated between two hydrophilic head groups (FIG. 1a), two hydrophobic tail groups (FIG. 1b), or between the two groups that link the head and tail portions of the surfactant components, (FIG. 1c). In this embodiment, the anionic, cationic and nonionic head groups applicable to the monomeric surfactants can also be used as head groups for Gemini surfactants bearing the degradable oligodienyl tail fragment(s). These linked surfactants can be identical or different in terms of chemical composition, head group type, and/or hydrophobic character. Each or both of the surfactant molecules comprising a Gemini surfactant can include any or all of the modifications described above. Moreover, the tethering group can contain a metathesis degradable fragment and can be oligiodienyl or alkenyl and can be fluorinated.

EXAMPLES

Figure 2:
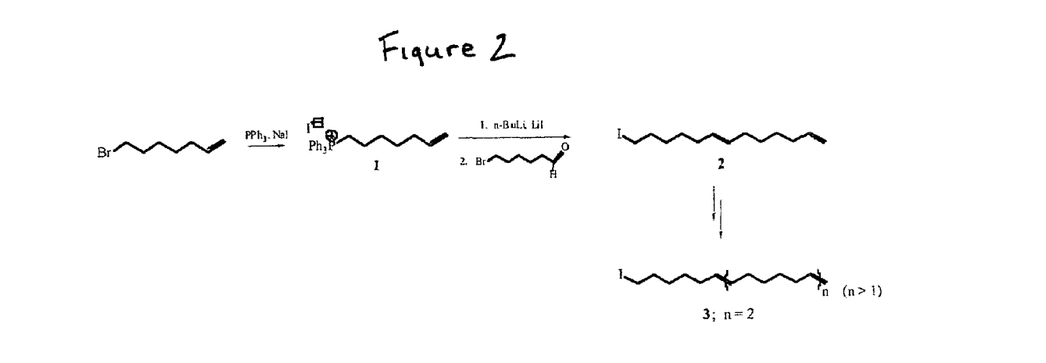
FIG. 2 shows a method for synthesizing an oligo-(1,6-hexadienyl) tail fragment.

In accordance with the present invention a surfactant molecule can be prepared by methods illustrated by the representative synthesis outlined in FIG. 2, which shows a synthesis for an oligo-(1,6-hexadienyl) surfactant tail fragment. Other synthetic strategies for generating double bond functionalities (dehydrations, dehydrohalogenations, other chemically- or thermally-induced eliminations, alkyne reductions) may be employed via conditions familiar to those skilled in the art.

As shown in FIG. 2, 1-heptenyl-7-triphenylphosphonium iodide 1 can be prepared from 7-bromo-1-heptene (other tertiary phosphine reagents may be employed). Subsequent Wittig condensation of the phosphorus ylide of 1 with 6-bromo-1-hexanal in the presence of LiI gave 13-iodotrideca-1,7-diene 2 as mainly the iodide containing 5-8% (by NMR and gas chromatography) of the 13-bromo endgroup. The presence of LiI exchanges the alkyl bromide endgroup for an iodide and encourages trans-alkene formation. This mixture was satisfactory to continue with a repetitive ylide formation/6-bromo-1-hexanal coupling to extend the hydrophobic tail precursor by one hexadienyl fragment each iteration.

Figure 3:
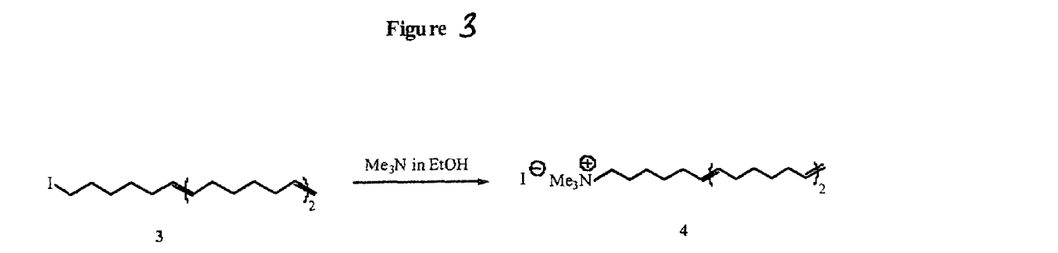
FIG. 3 shows a synthesis scheme for preparing a surfactant molecule.

FIG. 3 illustrates a method for attaching the polar surfactant head group to the oligo-(1,6-hexadiene) tail fragment. In the example shown, quaternization of trimethylamine using 19-iodononadeca-1,7,13-triene 3 generates cationic ammonium surfactant 4, trimethylnonadeca-6,12,18-trienylammonium iodide in 93% isolated yield.

Figure 4:
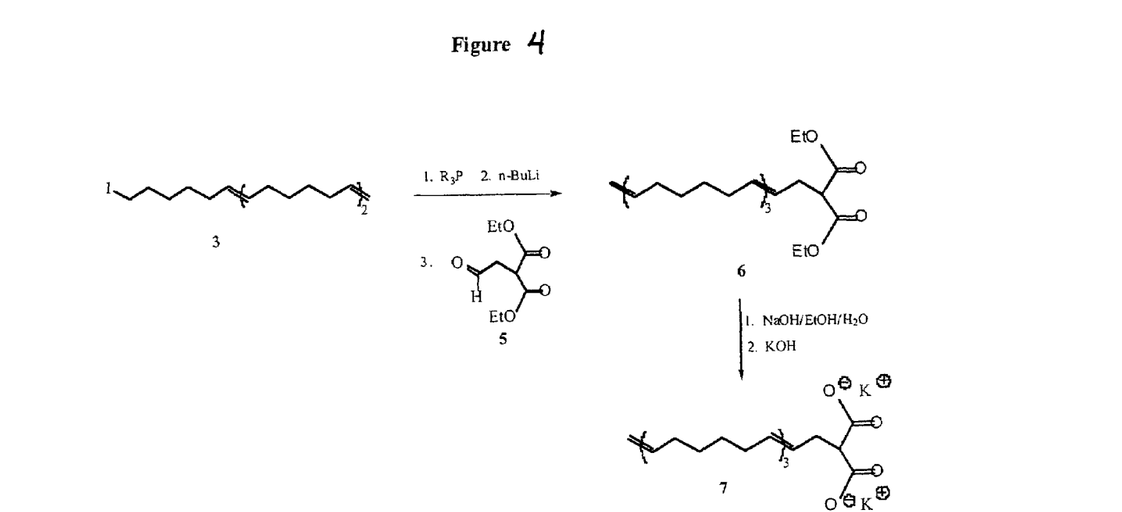
FIG. 4 shows a synthesis scheme for preparing a second surfactant molecule.

An example employing a derivatized malonate ester (FIG. 4) acts to illustrate the utility of employing a polyanionic head group and also serves as an example of a surfactant molecule designed to yield only small molecule remnants following surfactant degradation. This design feature is preferred for successfully generating volatile, easily removable degradation products. Iodide precursor 3 may also be converted to its phosphonium ylide using a tertiary phosphine followed by base deprotonation; Wittig coupling of the ylide with aldehyde-functionalized malonate ester 5 yields diethylester 6 in 33% isolated yield, which may be saponified to its parent dicarboxylic acid and subsequently deprotonated to the dicarboxylate salt 7 under conditions familiar to those practiced in the art.

Surfactants are characterized by determining the extent to which they exhibit surface-active properties. Two traditional methods are relied upon to achieve this: determining the extent to which the surfactant can solubilize a water-insoluble dye and its surface tension properties. The solubilization of a water-insoluble dye is used herein to confirm the presence of micellar aggregates in the present surfactant solution and to determine the critical micelle concentration ("cmc"), above which these aggregates form.

Figure 5:
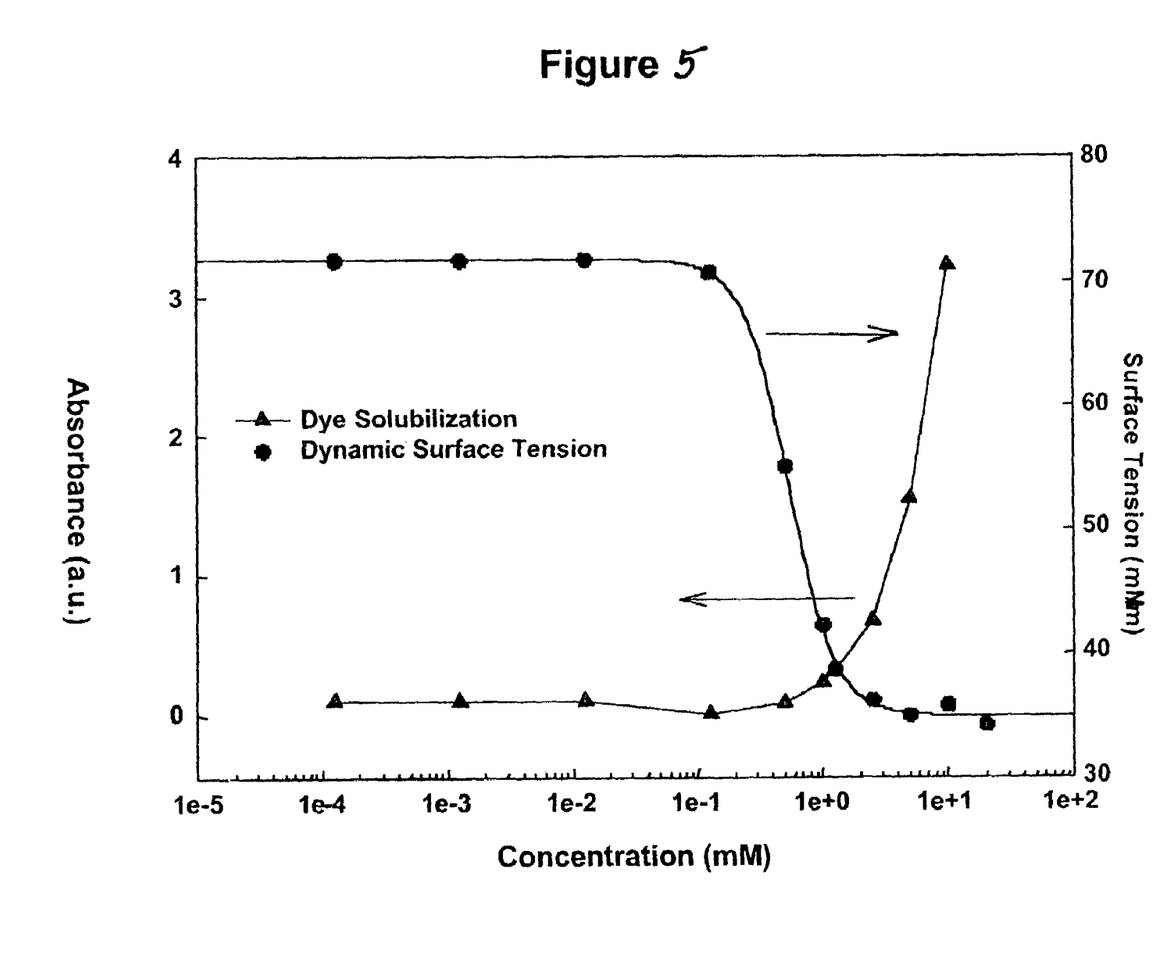
FIG. 5 is a semi-log plot of critical micelle concentration and dynamic surface tension of surfactant 3.
Figure 6:
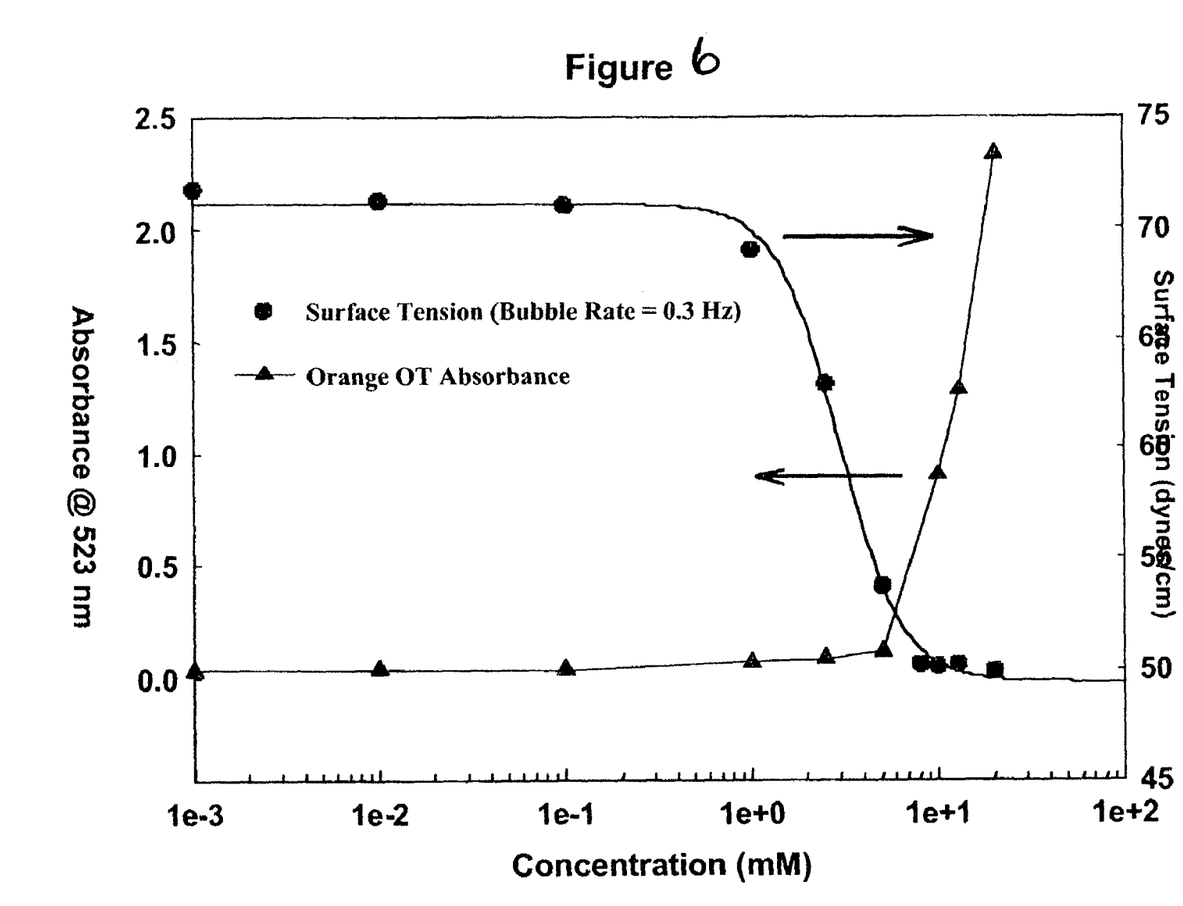
FIG. 6 is a semi-log plot of critical micelle concentration and dynamic surface tension of surfactant 7.

FIGS. 5 and 6 show plots of the absorbance values of the dye Orange OT used to investigate the enhanced solubility of a water-insoluble dye in the presence of micelles as a function of concentration for surfactants 4 and 7, respectively. The increase in absorbance of both dyes was monitored using the longest wavelength absorption at $\lambda$=523 nm for Orange OT. The measured absorbance values versus increasing dye concentration remain unchanged at low surfactant concentration then begin to increase through a short transition region after a characteristic surfactant concentration has been reached, followed by a linearly increasing set of measurements. The linearly increasing dependence indicates the presence of micelles and is attributed to the increase in the amount of dye that is solubilized in the micellar cores of the surfactants. Critical micellar concentration, therefore, is defined as the intersection of lines fit to the set of points in the constant absorbance range (at low surfactant concentration) and the linearly increasing set of measurements for each surfactant system. The cmc values determined by the dye solubilization method for surfactant 4 is 1.2 mM, and for 7 the cmc is 4.7 mM.

FIGS. 5 and 6 also show the response of dynamic surface tension values (operated in equilibrium mode) measured as a function of concentration for surfactants 4 and the anionic salt 7 in aqueous solution. The physicochemical properties of a surfactant change to a significant degree after reaching the cmc due to the presence of micelles and a surfactant-saturated air-water interface.

TABLE 1

Physicochemical Properties of the Surfactants

| Surfactant | cmc[a] (mmol) | cmc[b] (mmol) |
|---|---|---|
| 4 | 1.2 | 1.9 |
| 7 | 4.7 | 5.9 |

Figure 7:
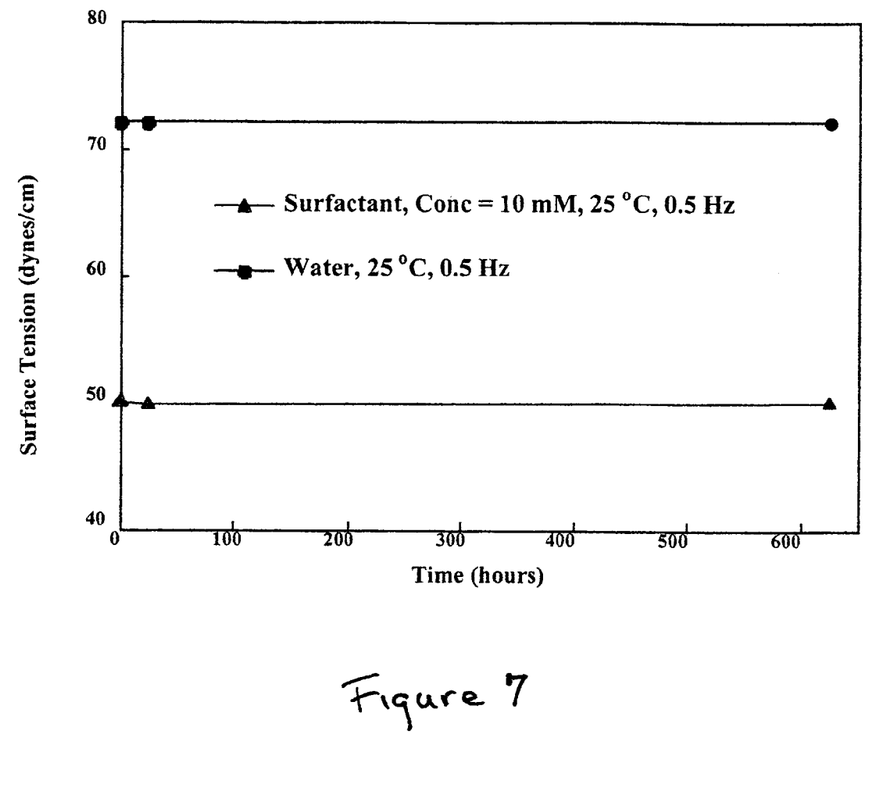
FIG. 7 shows the dynamic surface tension measurements for a 10 mM aqueous solution of bis-carboxylate surfactant 7.

[a]As determined by Orange OT dye solubilization
[b]As determined by surface tensiometry A comprehensive listing of all the physicochemical properties calculated for these surfactants is shown above in Table 1. As seen in FIGS. 6 and 7, both embodiments of the surfactant examples exhibit the classical dependence of surface tension as a function of concentration, whereby a constant surface tension region (approximately that of water) at low surfactant concentrations transitions smoothly to an intermediate concentration range in which surface tension decreases linearly, ultimately transitioning into a region having a relatively constant surface tension, reduced from that of water, at higher surfactant concentration.

The surfactant concentration at the intersection of the two lines which are least-squares fit to (1) the rapidly changing surface tension readings and (2) the low, relatively constant surface tension readings at high surfactant concentrations defines the cmc by this method. The cmc's calculated from the surface tension data of surfactants 4 and 7 are 1.9 mmol and 5.9 mmol, respectively. The higher values for cmc as determined by dynamic surface tension compared to Orange OT dye solubilization can be attributed to static (dye solubilization) vs. dynamic (surface tension) measurements of the microenvironment.

To determine the stability of these surfactants in solution, a room temperature aging study was conducted for each. The results, shown in FIG. 8, indicate that the surface tension values remain relatively constant for both surfactants over an extended time period (580 hrs) and do not suffer significant degradation.

As discussed above, the invention discloses a novel class of surfactant molecules that possess a structure that can be readily decomposed by ring-closing metathesis, and particularly by the action of a transition metal catalyst, to form small molecule products that have increased volatility and/or enhanced solubility as compared to the original surfactant molecule and are thus easily removable by solvent extraction or vacuum extraction at low temperature.

Figure 8:
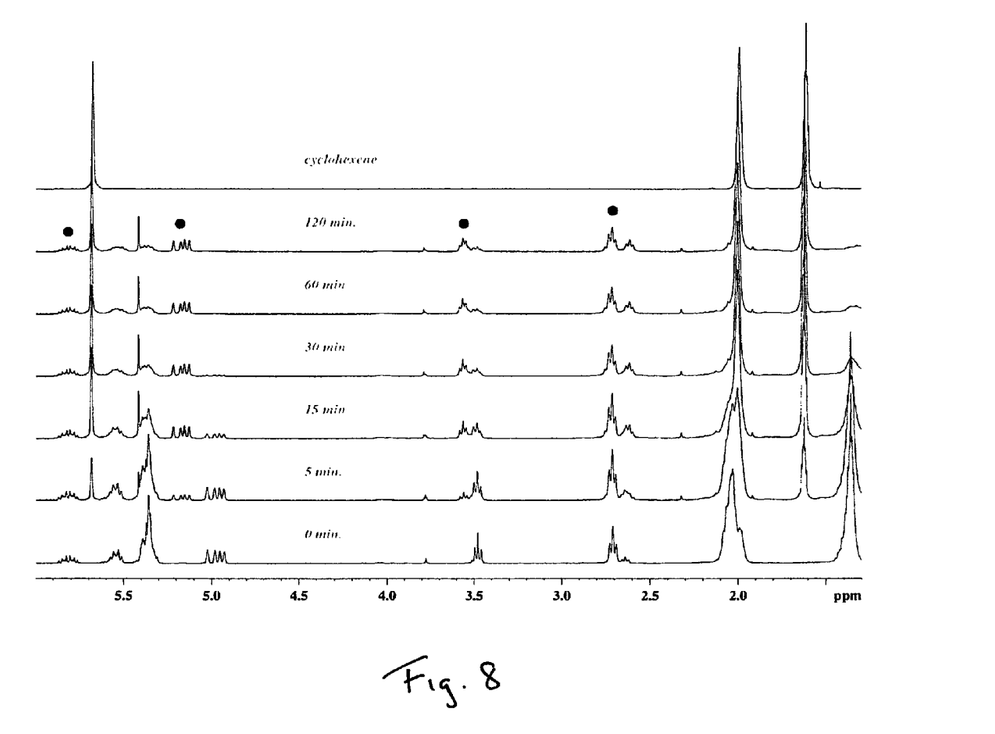
FIG. 8 shows the time evolved $^1$HNMR spectra of a chloroform solution of cationic ammonium surfactant 4 resulting from addition of metathesis catalyst $RuCl_2$ $[C_{21}H_{26}N_2]$ $[CHC_6H_5]P(C_6H_{11})_3$.

Decomposition of these surfactant molecules takes place by the action of a ring closing metathesis-active transition metal catalyst on the tail portion of the surfactant, as illustrated in FIG. 8. It is believed that initiation of the decomposition reaction produces styrene. Intramolecular reaction of double bonds further up the tail group produces cyclohexene faster than cross-metathesis with another surfactant.

Known active catalyst systems include discreet homogeneous or supported mononuclear late transition metal alkylidenes; in a preferred embodiment, the catalyst system is a ruthenium-based benzylidene. Other mononuclear catalysts, including high oxidation state early transition metal systems capable of acting alone as ring closing metathesis agents are included as possible degradation agents. Such high oxidation state catalysts include those derived from molybdenum or tungsten. Furthermore, mononuclear catalysts which are active in the presence of external olefins to induce surfactant degradation in an acyclic diene metathesis (ADMET) depolymerization sense are included. Also, homobimetallic, heterobimetallic and ternary catalyst systems known to promote ring closing metathesis or ADMET depolymerization of organic polyenes are claimed to enable surfactant degradation.

Figure 9:
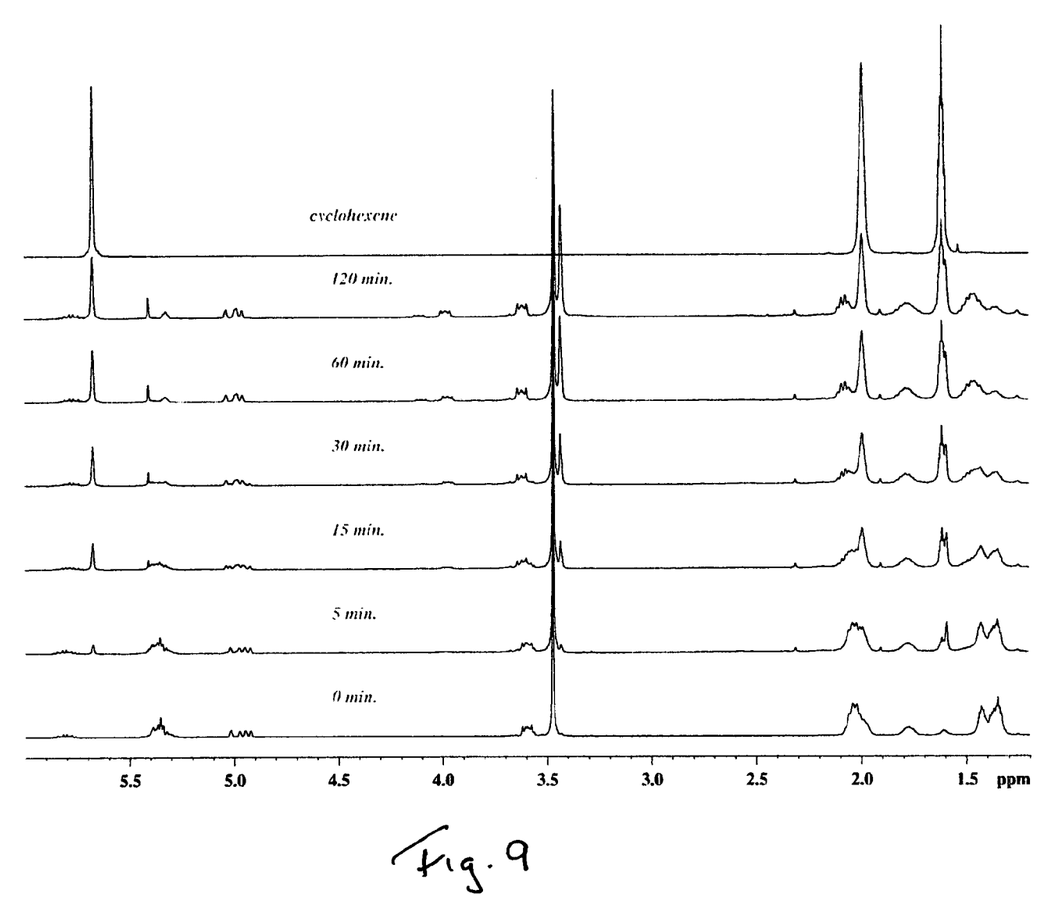
FIG. 9 shows the time evolved $^1$HNMR spectra of a chloroform solution of the free acid form of surfactant 7 resulting from addition of metathesis catalyst $RuCl_2$ $[C_{21}H_{26}N_2][CHC_6H_5]P(C_6H_{11})_3$.

Demonstration of the metathesis degradative reactivity of 4 and 7 is shown in FIGS. 8 and 9. $^1$H NMR spectroscopy of a chloroform solution of 4 in the presence of 2 mol. % of $RuCl_2[C_{21}H_{26}N_2][CHC_6H_5]P(C_6H_{11})_3$ (CAS [246047-72-3]), often referred to as the "$2^{nd}$ generation Grubbs catalyst", indicates nearly complete decomposition of 4 within 60 min. at 25° C. Cyclohexene formation is clearly evident in the solution within five minutes of adding the catalyst, as evidenced by the appearance of broad singlets at $\delta$=1.62 and 1.97 ppm and a characteristic singlet at $\delta$=5.67 ppm.

$^1$H NMR also indicates the presence of the former head group as 7-(N,N,N-trimethylammonium)hept-1-enyl iodide (unchanged chemical shift at $\delta$=3.48 ppm from starting surfactant 4) as well as the cross-coupled product, cis/trans-1,12-bis(trimethylammonium)dodec-6-enyl diiodide (equivalent methyls at $\delta$=3.43 ppm). Chloroform extraction of the resulting aqueous solution indicates that cyclohexene was the only organic soluble product of the degradation.

To demonstrate the controlled and mild decomposition of 7 via ring-closing metathesis, a $^1$H NMR experiment was performed on a chloroform solution of free acid 6. In the presence of 2 mol. % of $RuCl_2[C_{21}H_{26}N_2][CHC_6H_5]P(C_6H_{11})_3$ nearly complete decomposition of the free acid surfactant is observed in an hour at room temperature. Within 5 minutes after the introduction of catalyst, cyclohexene was clearly present in solution as evidenced by the appearance of broad singlets at $\delta$=1.62 and 1.97 ppm and a characteristic singlet at $\delta$=5.67 ppm (see FIG. 10).

Additionally, peaks clearly assignable to allyl malonic acid ($\delta$=5.12-5.22 ppm, $\delta$=3.57 ppm, $\delta$=2.68 ppm) were present, by comparison with an authentic sample. Surfactant decomposition was also successful using $RuCl_2(CHC_6H_5)$

[P(C$_6$H$_{11}$)$_3$]$_2$ (CAS [172222-30-9]); however, the decreased solution half-life of the first generation catalyst does not allow for complete decomposition before the catalyst itself decomposes. Addition of a second aliquot of the first generation catalyst completes the decomposition.

From the foregoing description and examples, one skilled in the art can readily ascertain the essential characteristics of the present invention. The description and examples are intended to be illustrative of the present invention and are not to be construed as limitations or restrictions thereon; the invention being delineated in the following claims.

We claim:

1. A surfactant of formula (1),

(1)

wherein

A is a hydrophilic head group or a polar head group, wherein the polar head group is alkoxide, alkyl sulfide, phenolate, thiophenolate, carboxylate, sulfate, sulfonate including sulfated polyethylenated alcohol, sulfated triglyceride, sulfosuccinate, phosphate, phosphonate, polyphosphonate, carbonate, borate, —NR'R"R"'+, —P R'R"R"'+, —SR'R"+, guanidinium, pyridinium, or other quaternized heterocyclic amines, wherein R', R", R''' each represent hydrogen or any aliphatic, cyclic or aromatic organic group, with or without further substitution, polyoxyethylenated alkyl phenol, tertiary acetylenic glycol, pyrrolidone, alkylglycoside, or a zwitterion;

B is a linker, comprising at least one alkyl or aryl group; and

C is an unsaturated hydrocarbon tail, wherein C is represented by (2), (2)

wherein R$^1$, R$^2$, R$^3$, and R$^4$ are the same or different and are hydrogen, straight or branched chain alkyl groups that can contain heteroatom functionalities, or cyclic alkyl chains; n is at least 2; a is 1 to 6; m is equal or greater than 1; and p is at least 1.

2. The surfactant of claim 1, wherein R$^1$ and R$^2$ are straight or branched chain alkyl groups.

3. The surfactant of claim 2 wherein either or both R$^1$ and R$^2$ contain a heteroatom.

4. The surfactant of claim 2, wherein the alkyl groups contain at least one singly substituted aromatic group and wherein the singly substituted aromatic group contains one heteroatom.

5. The surfactant of claim 1, wherein B is unsubstituted (CH$_2$)$_r$ or a branched (CRR')$_n$ linear or cyclic alkyl chain, wherein n>0.

6. The surfactant of claim 1, wherein B is an unsubstituted or substituted aromatic ring.

7. The surfactant of claim 6, wherein A and C are ortho, meta- orpara- about B.

8. The surfactant of claim 1, wherein B is substituted by at least one fluorine substituent.

9. The surfactant of claim 1, wherein B comprises a chain of two or more unsubstituted or multiply substituted aromatic rings, wherein substitution is alkyl or heteroatom-containing alkyl or combinations thereof.

10. The surfactant of claim 1, wherein the tail group C is a metathesis-active organic moiety.

11. The surfactant of claim 10, wherein the tail group is oligo-(1,5-pentadienyl), oligo-(1,6-hexadienyl) or oligo-(1,7-heptadienyl) that can be unsubstituted or substituted, wherein the substitutions are straight chain alkyl or branched alkyl groups, straight chain alkyl or branched alkyl groups containing heteroatoms, unsubstituted or multiply substituted aromatic groups, unsubstituted or multiply substituted aromatic groups containing heteroatoms.

12. The surfactant of claim 10, wherein the tail group is fluorinated.

13. A surfactant comprising two spaced apart surfactants according to claim 1, wherein the two surfactants are covalently bonded through a tethering group, wherein the tethering group bonds either both head groups, both linker groups, or both tail groups of said surfactant together and wherein said spaced apart surfactants are the same or different.

14. The surfactant of claim 13, wherein the tethering group contains a metathesis degradable moiety.

15. The surfactant of claim 13, wherein the tethering group is oligiodienyl or alkenyl.

16. The surfactant of claim 13, wherein the tethering group is fluorinated.

17. The surfactant of claim 13, wherein the head group of at least one of the component surfactant molecules is a polar head group.

18. The surfactant of claim 13, wherein at least one linker group is an aromatic group.

19. The surfactant of claim 18, wherein the aromatic group is substituted and wherein the substitution is alkyl or heteroatom-containing alkyl.

20. The surfactant of claim 18, wherein the head groups and the tail groups are arranged ortho, meta- orpara- about the linker groups.

21. The surfactant of claim 13, wherein at least one linker group comprises a chain of two or more aromatic groups.

22. The surfactant of claim 21, wherein at least one of the aromatic groups contains at least one substitution, wherein the substitution is alkyl or heteroatom-containing alkyl.

23. The surfactant dipotassium heneicosa-2,8,14,20-tetraenyl malonate.

24. The surfactant 13-(triphenylphosphonium)trideca-1,7-dienyl iodide.

25. The surfactant 19-(triphenylphosphonium)nonadeca-1,7-dienyl iodide.

26. The surfactant 19-(N,N,N-trimethylammonium)nonadeca-1,7,13-trienyl iodide.

* * * * *